United States Patent
Sengupta et al.

(10) Patent No.: US 8,187,890 B2
(45) Date of Patent: May 29, 2012

(54) RAPID SENSING OF TOXIC METALS WITH HYBRID INORGANIC MATERIALS

(75) Inventors: Arup K. Sengupta, Bethlehem, PA (US); Prasaun K. Chatterje, Bethlehem, PA (US)

(73) Assignee: Lehigh University, Bethlehem, PA (US)

( * ) Notice: Subject to any disclaimer, the term of this patent is extended or adjusted under 35 U.S.C. 154(b) by 19 days.

(21) Appl. No.: 12/602,523

(22) PCT Filed: Jun. 4, 2008

(86) PCT No.: PCT/US2008/065706
§ 371 (c)(1),
(2), (4) Date: Dec. 1, 2009

(87) PCT Pub. No.: WO2008/151208
PCT Pub. Date: Dec. 11, 2008

(65) Prior Publication Data
US 2010/0178704 A1    Jul. 15, 2010

Related U.S. Application Data

(60) Provisional application No. 60/941,769, filed on Jun. 4, 2007.

(51) Int. Cl.
*G01N 33/20* (2006.01)

(52) U.S. Cl. .................. 436/80; 436/73; 436/81

(58) Field of Classification Search ............... 436/80, 436/81, 73
See application file for complete search history.

(56) References Cited

U.S. PATENT DOCUMENTS
5,186,830 A * 2/1993 Rait ................. 210/232

OTHER PUBLICATIONS

A New Hybrid Inorganic Sorbent for Heavy Metals Removal Yi-Min Gao, Arup K. Sengupta, and Dale Simpson Water Research vol. 29, No. 9, pp. 2195-2205.*

* cited by examiner

*Primary Examiner* — Robert J Hill, Jr.
*Assistant Examiner* — Dwan A Gerido
(74) *Attorney, Agent, or Firm* — Design IP (57) ABSTRACT

Methods for rapid sensing of dissolved toxic heavy metals use a hybrid inorganic material ("HIM"), which is synthesized from hydrated iron oxide ("HFO") and calcium magnesium silicate. HIM thus synthesized is used in sensing dissolved toxic heavy metals. Water containing toxic heavy metals (e.g., lead, copper, zinc, nickel, etc.) is passed through a sorbent bed of HIM, whereupon it shows a sharp drop in pH after a certain length of time. The presence of HFO and calcium magnesium silicates in HIM synergistically provide a precipitous drop in pH, which is characteristic of the concentration and type of toxic heavy metal. Therefore, observing a change in pH indicates the presence and identity of heavy metal ions in a test water sample.

20 Claims, 10 Drawing Sheets

| pH | 6.9 | 7.3 | 7.85 | 8.6 | 8.7 | 8.9 |
|---|---|---|---|---|---|---|
| Zn(II) mg/L | 0.18 | 0.12 | 0.07 | ND | ND | ND |
| color | colorless | colorless | colorless | pink | pink | dark pink |

(ND = Not Detected)

RAPID SENSING OF TOXIC METALS WITH HYBRID INORGANIC MATERIALS

CROSS-REFERENCE TO RELATED APPLICATIONS

This application claims the priority of copending U.S. patent application No. 60/941,769, filed Jun. 4, 2007, the entire contents of which are incorporated herein by reference.

FIELD

This application describes hybrid inorganic materials, methods of their manufacture, and uses thereof in the detection of toxic heavy metal ions in water samples.

BACKGROUND

Simple and quick detection of heavy metals in water is essential for numerous applications, particularly due to the increasing global threat of heavy metal contamination of water because of anthropogenic activities including environmental pollution. Some heavy metals are essential nutrients at trace concentration, but all of them pose serious health threats beyond the regulated level. Therefore, the importance of understanding the presence and concentration of heavy metal in water is enormous.

Available heavy metal sensing devices, such as metal selective electrode based devices, enzyme based sensor (biosensor), chelating agent based sensors, and the like have unsuitable selectivity and sensitivity. Furthermore, they typically are only useful under laboratory conditions because of their its functional complexities. Traditional sensors equipped with mercury-based electrodes and measuring instruments have short service lifetimes, and they often require pretreatment or modification of samples. Therefore, the process of measurement is slow and not precise. Efforts for toxic heavy metal detection through enzyme based sensors or bio-sensors, as well as other polymeric and chelating agent based sensors, have seen little practical success. In addition, commercially available heavy metal analyzers based on electrochemical techniques requires sample preparation and lack in rapid detection, portability, and sensitivity.

Likewise, advanced heavy metal analyzers including atomic absorption spectrometers and inductively coupled plasma spectrometers are suitable for precise and detailed laboratory level analysis only. Therefore, practical devices suitable for rapid, real-time sensing of different toxic heavy metals dissolved in water for in-field applications, particularly in remote areas or developing nations with a dearth of analytical laboratories, are not presently available. As a result, there is a long-standing unmet demand for operationally simple, rapid and useful heavy metal sensing and detection devices, systems, materials, and methods that are free of the above-noted deficiencies.

SUMMARY

Described herein are new methods for rapid sensing of dissolved toxic heavy metals using a synthesized hybrid inorganic material ("HIM"). The methods require only measuring a pH change, and therefore they may be readily implemented in non-laboratory field situations. HIM is synthesized from hydrated iron oxide ("HFO") and calcium magnesium silicate in certain proportions, followed by chemical-thermal processing in graphite furnace where the mixture is subjected to different level of temperature with different residence time. HIM thus synthesized is used in sensing dissolved toxic heavy metals. Toxic heavy metals (e.g., lead, copper, zinc, nickel, etc.) in water, when passed through a sorbent bed of HIM, show a sharp drop in pH. Therefore, observing a change in pH indicates the presence and identity of heavy metal ions in a test water sample.

The presence of HFO and calcium magnesium silicates in HIM synergistically provide a precipitous drop in pH, which is characteristic of the concentration and type of toxic heavy metal. During operation, calcium magnesium silicate releases hydroxyl ions through hydrolysis causing the pH to become alkaline, while on the other hand hydrated iron oxide present in HIM acts as good adsorbent and binds heavy metals through Lewis acid-base interactions. The presence of both components act synergistically so that breakthrough of heavy metal from the HIM sorbent bed coincides with a sharp drop in pH that is correlated to the concentration and type of heavy metal. A sharp drop of pH indicates the presence of a heavy metal, which can also be observed through a change in color of an indicator solution or pH paper. By varying ratio of hydrated iron oxide and alkaline metal silicate in the HIM, time and magnitude of response with respect to pH can be controlled for individual heavy metals.

Additional features may be understood by referring to the accompanying drawings, which should be read in conjunction with the following detailed description and examples.

DESCRIPTION OF THE DRAWINGS

FIG. 7 is a plot showing how pH at the exit of column changed when zinc of 1.0 mg/L was present in feed water

[Na(I)=100 mg/L, Ca(II)=20 mg/L, Zn(II)=1.0 mg/L, pH=5.1, EBCT=0.16 min]. The drop in pH, left axis, represented by diamonds (♦), occurred earlier when compared to the case when zinc was present in influent at a concentration of 0.5 mg/L. The concentration of Zn(II) in eluent water is plotted along the right axis, and it is represented by squares (■). The horizontal axis is bed volume (BV).

DETAILED DESCRIPTION AND EXEMPLARY EMBODIMENTS

Synthesized hybrid inorganic materials may be used to sense or detect the presence of toxic heavy metals such as zinc, copper, lead, nickel, and others dissolved in water by simply measuring pH or color changes. As used herein, the term "hybrid inorganic material" ("HIM") is meant to include any mixture of hydrated iron (e.g., Fe(III)) oxides ("HFO") and calcium magnesium silicate (also known as akermanite), which has been synthesized at elevated temperature, e.g., in a graphite furnace.

Such heavy metal detection methods exploit the process whereby calcium magnesium silicate undergoes hydrolysis thereby producing slightly alkaline pH when exposed to a test water sample, and HFO selectively bind heavy metals through Lewis acid-base interactions. Water contaminated with heavy metal, upon passing through a bed of HIM, shows a significant drop in pH coinciding with the breakthrough of heavy metal. The drop in pH is characteristic of the concentration and the type of toxic metal.

Aside from a simple pH meter or another readily available pH indicator (e.g., phenol-phthalein), no other instrument or specialty chemicals are required. A change in color of an indicator solution or pH paper is even useful to sense the presence of heavy metal. Accordingly, in an advantageous application, a method is provided herein for detecting or sensing toxic heavy metals dissolved in water by a rapid, simple, inexpensive, and extremely useful new technique.

Accordingly, in an example embodiment, a method of detecting a heavy metal contaminant in water includes steps of (1) passing a water sample through a hybrid inorganic material containing heat-treated fused particles of hydrated iron oxide and calcium magnesium silicate; and thereafter (2) detecting a pH change in the water sample. The example, the pH change may be an increase in pH. Likewise, the pH change may be a change in the slope of the pH curve versus water volume (e.g., dpH/dBV). Such a pH change is indicative of a presence of at least one a heavy metal, or the pH change is indicative of a concentration of at least one heavy metal (the magnitude of the pH change being characteristic of certain metals). The heavy metal contaminant may include at least one heavy metal such as copper, lead, zinc, cadmium, or nickel; although typically the heavy metal is not an alkali metal or an alkaline earth metal.

In a typical embodiment, the hybrid inorganic material is in the form of a particulate packed into a bed through which water is capable of flowing. As described elsewhere herein, the water sample is suspected of containing at least one dissolved heavy metal contaminant. The flow of the water sample through the hybrid inorganic material may be controlled by mechanical means (e.g., a pump, which may be operated manually or by means of an electric pump), or the flow of the water sample through the hybrid inorganic material may be controlled by gravity filtration. Often, the water (or a sample thereof) is intended for human, animal, or agricultural use.

In yet another embodiment, a method of making a hybrid inorganic material includes steps of (1) rapidly heating a mixture of hydrated iron oxide and calcium magnesium silicate to thereby produce heat-treated fused particles of hydrated iron oxide and calcium magnesium silicate, followed by (2) rapidly cooling the mixture. For example, the mixture may be heated to about 1800° C. and cooled to about room temperature in less than about two minutes. Such a method of making a hybrid inorganic material may also include a step of, after heating and cooling, grinding or pulverizing the mixture to thereby produce heat-treated fused particles of hydrated iron oxide and calcium magnesium silicate. Additionally, the method may include a further step of rinsing the heat-treated fused particles with deionized water, as well as a step of packing the heat-treated fused particles into a bed through which water is capable of flowing. As noted previously herein, an example ratio of the hydrated iron oxide to the calcium magnesium silicate is about 30:70 by mass.

In still yet another embodiment, a hybrid inorganic material consisting essentially of heat-treated fused particles of hydrated iron oxide and calcium magnesium silicate, with only small quantities of other components, which do not substantially interfere with the operation of the hybrid inorganic material. The hybrid inorganic material according to claim 19, wherein the hydrated iron oxide and the calcium magnesium silicate are present in a ratio of about 30:70 by mass.

Synthesis of Hybrid Inorganic Material ("HIM")

Hybrid inorganic materials may prepared from two different inorganic starting materials, which are subjected to thermal-chemical synthesis techniques. For example, predetermined amounts or proportions of hydrated iron oxide and calcium magnesium silicate are mixed thoroughly. The mixture is then put into graphite furnace and subjected to different temperatures for different durations of time for the purposes of drying, heating, fusing, and cooling the mixture. Materials thus produced are ground, rinsed in deionized water, and dried for subsequent use.

This synthesis method allows mixing and fusion of two component materials, i.e., hydrated iron oxide and calcium magnesium silicate, in preselected or controllable proportions. By varying proportion of component materials, the adsorption capacity of HIM can be varied. Additionally, by varying the ratio of hydrated iron oxide and alkaline metal silicate in HIM, the time and magnitude of response with respect to pH can be controlled for individual heavy metals.

Figure 1:
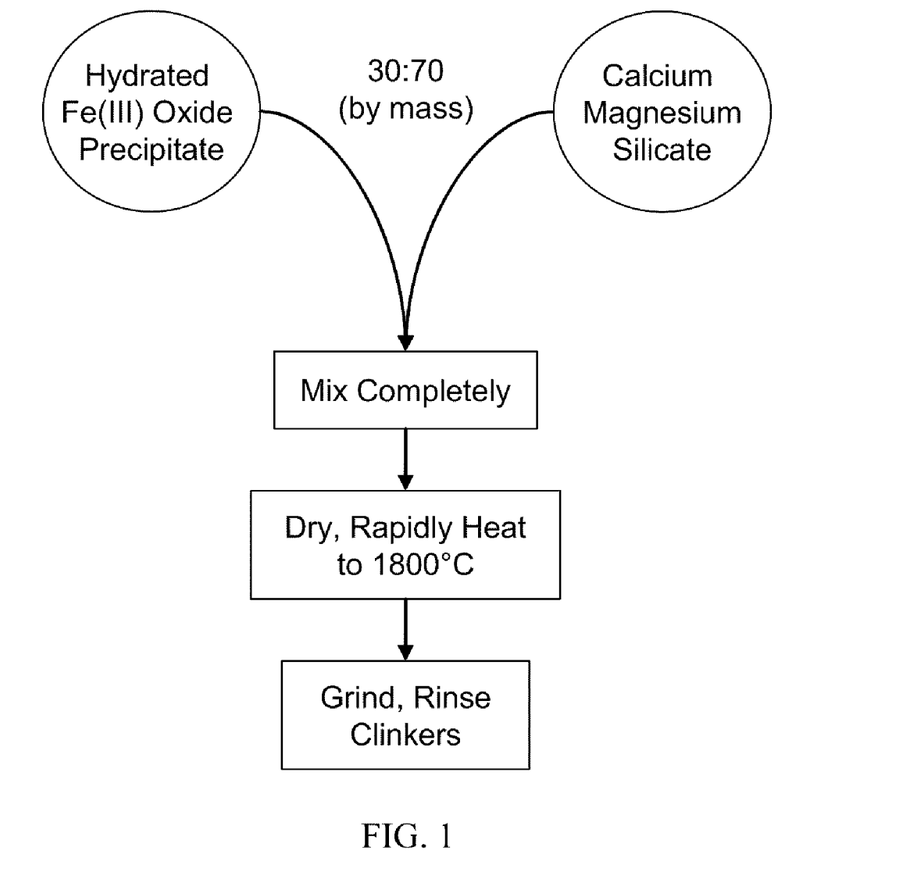
FIG. 1 illustrates a schematic diagram of a step-wise procedure for the synthesis of a hybrid inorganic material ("HIM") in accordance with an example embodiment hereof.

Referring to FIG. 1, which includes a flowchart illustrating example steps for synthesis of HIM, freshly prepared precipitates of ferric hydroxide (hydrated iron oxide) are mixed with ground amorphous calcium magnesium silicate ($Ca_2MgSi_2O_7$), which may be purchased from Ward Earth Science Co. in Rochester, N.Y., in the proportion of 30:70 (HFO to calcium magnesium silicates) by mass. The mixture is dried and rapidly heated to 1800° C. in a graphite furnace, which causes fusion of the particulate starting materials, followed by quickly cooling to 30° C., which leads to formation of clinkers (partially vitrified masses of thermally fused material). An example heating/cooling temperature program is as follows:

| Temperature (C.) | Time (sec) | Function |
|---|---|---|
| 30-200 | 20 | Drying |
| 200-700 | 30 | Preheating |
| 700-1800 | 25 | Fusion |
| 1800-30 | 40 | Cooling |

The clinkers are subsequently ground (e.g., to produce an average particle size of from about 100 to about 200 μm) and rinsed with deionized ("DI") water prior to use in sensing of heavy metals.

Application of HIM to Heavy Metal Sensing

Figure 2:
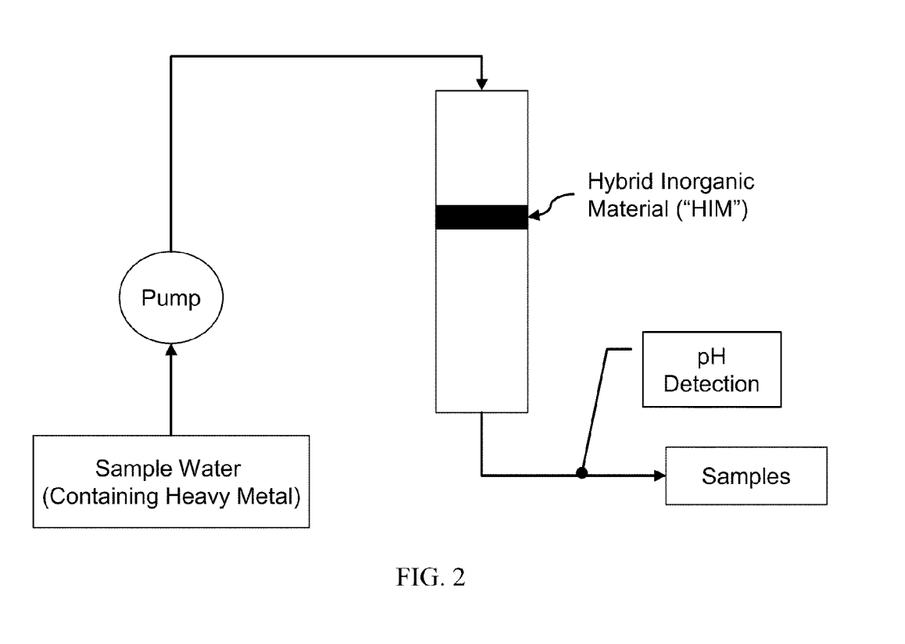
FIG. 2 illustrates a schematic representation of an experimental set-up using a hybrid inorganic material ("HIM") for sensing dissolved heavy metals according to an example embodiment hereof. A typical empty bed contact time ("EBCT") is from about 10 sec to about 15 sec.

As illustrated in FIG. 2, a primary use of HIM is to sense or detect the presence of dissolved heavy metals in water through a surrogate pH change. Additionally HIM acts as adsorbent for separation of dissolved heavy metals. Hydrated iron oxide is a known to be a good adsorbent for various heavy metals like lead, copper, zinc, cadmium, nickel, etc. at alkaline pH (8 or more) and adsorption decreases sharply as pH goes down below 7. Calcium magnesium silicate ($Ca_2MgSi_2O_7$), on the other hand releases hydroxyl ions through incongruent dissolution according to the following reaction:

$$\overline{Ca_2MgSi_2O_7} + 3H_2O \longleftrightarrow 2\overline{SiO_2} + 2Ca^{2+} + Mg^{2+} + 6OH^- \quad (1)$$

The over bar denotes the solid phase. The hydrolysis of calcium magnesium silicate produces alkaline pH (remains in the vicinity of 9.0) and at this alkaline pH, hydrated iron oxide exhibit high sorption affinity for the heavy metals through formation of inner-sphere complexes according to Lewis acid-base interactions. No precipitation of heavy metals is observed at concentrations less than about 2 mg/L. As sample water is passed through a mini-column containing HIM, the target toxic metal (e.g., zinc, nickel, or copper) is selectively sorbed onto HFO while the hydrolysis of akermanite continues to show steady alkaline pH at the exit of the column. Although the HIM is depicted in FIG. 2 as being contained within a column through which water is pumped, it may be used in other configurations, such as a filtration media, cartridges, and the like.

When toxic metal breakthrough from the column occurs, exit pH immediately drops due to the rapid formation of metal-hydroxy complexes, i.e., dissipation of hydroxyl ions in accordance with the following reaction:

$$Me^{2+} + nOH^- \longleftrightarrow [Me(OH)_n]^{2-n} \quad (2)$$

Because of the formation of metal hydroxyl complexes, the availability of free hydroxyl ion decreases causing a drop in pH, which may be observed through change of color of indicator solution or pH paper. Breakthrough of different heavy metals occur at different times because of their difference in sorption affinity towards HFO binding sites. Furthermore, the slope of the pH curve with respect to volume of heavy metal laden water provides a peak that is characteristic of the type and concentration of individual heavy metals.

Commonly encountered alkaline earth metals such as sodium and calcium have no impact on pH, and the ubiquitous presence of these ions in potable water sources does not interfere with the heavy metal detecting characteristics of the material. Only in the presence of heavy metals does a sharp drop in pH occur.

Other advantages and novel features hereof will be apparent from the following Examples, which should not be construed as limiting.

EXAMPLES

Several fixed bed column runs were carried out using HIM as bed material. FIG. 2 shows a schematic representation of the experimental set-up. At the exit of the column, pH was measured and samples were collected in a fraction collector for analysis of heavy metal concentration. Hydrodynamic parameters such as flow rate, empty bed contact time, and the like were maintained consistently (almost identical) for different runs. For example, the empty bed contact time ("EBCT") ranged from about 10 sec to about 15 sec. In order to validate impact of heavy metals, experiments were carried out to ascertain (1) the influence of commonly encountered alkaline earth metals like sodium and calcium, as well as the influence of deionized ("DI") water; and (2) the influence of heavy metals dissolved in water in the presence of other potential interfering ions like sodium, calcium, etc., which are commonly present in potable water.

Figure 3:
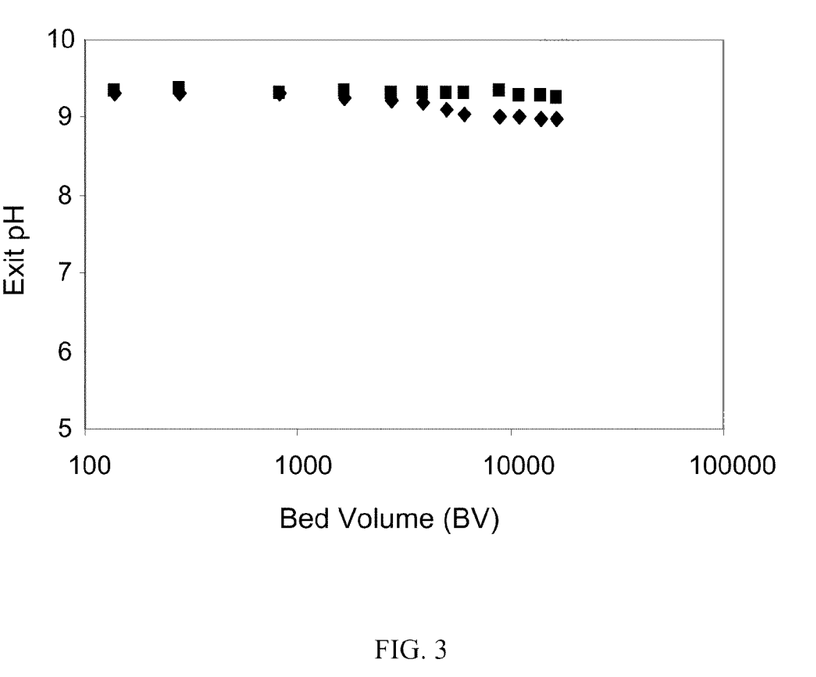
FIG. 3 is a plot showing pH around 9 at the column exit in the absence of heavy metal. Changeover to deionized ("DI") water showed no impact on pH. Saline influent [Na(I)=100 mg/L, Ca(II)=20 mg/L, pH=5.4, EBCT=0.2 min] is represented by diamonds (♦), and deionized water influent is represented by squares (■). The vertical axis is pH, and the horizontal axis is bed volume ("BV").

FIG. 3 demonstrates that in the presence of commonly encountered electrolytes, the pH at the exit of the mini-column stays slightly alkaline (around 9.0) and turns pink through the addition of phenolphthalein indicator solution. (Phenolphthalein turns colorless in acidic solutions and pink in alkaline solutions). Fluctuations in the concentration of alkaline and alkaline earth metal cations (e.g., $Na^+$, $K^+$, $Ca^{2+}$, and $Mg^{2+}$) or changeover to deionized water did not show any significant effect on the exit pH.

Figure 4:
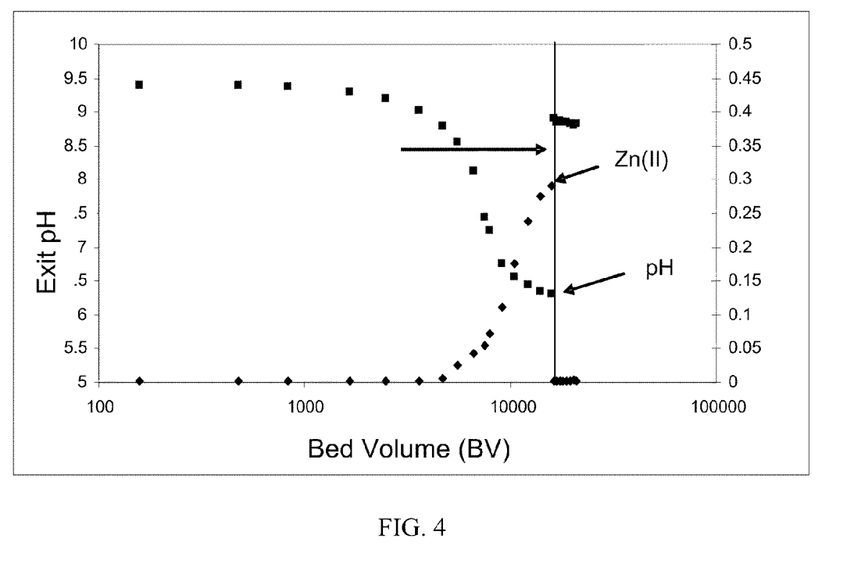
FIG. 4 is a plot showing a significant drop in pH, left axis, represented by squares (■), in the presence of zinc in the influent feed water [Na(I)=100 mg/L, Ca(II)=20 mg/L, Zn(II)=0.5 mg/L, pH=5.1, EBCT=0.16 min]. The concentration of Zn(II) in eluted water ranged from 0.0 mg/L to 0.5 mg/L, right axis, represented by diamonds (♦). The horizontal axis is bed volume ("BV"). Note that the exit pH returned to almost the initial value when feed water was replaced by DI water (solid vertical line).

The plot in FIG. 4 illustrates how the exit pH of the column effluent sharply dropped from 9.0 to 6.5 when zinc of 0.5 mg/L was present in the influent. The drop in pH coincided with zinc ion breakthrough from the column. When the influent was later replaced by deionized water (solid vertical line), exit pH almost returned to the initial value indicating presence of heavy metal is the cause for drop in pH.

Figure 5:
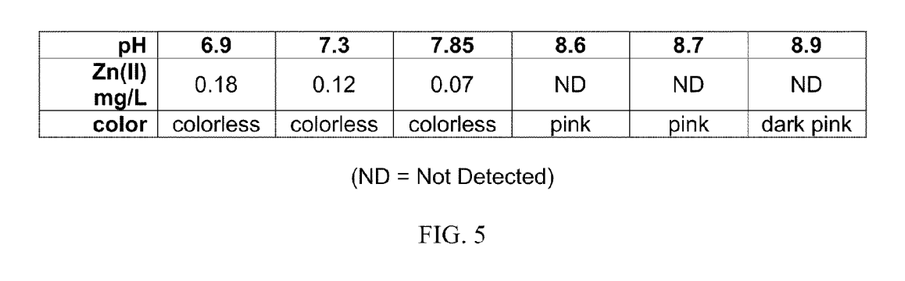
FIG. 5 depicts results from an experiment in which phenolphthalein indicator solution turned from pink to colorless as zinc started to elute from the exit of the column.

The data in FIG. 5 demonstrate change of color of phenolphthalein indicator solution, which turned from pink to colorless as pH decreased, whereas at the same time zinc started to show up gradually at the exit of the column. This demonstrates that color change of an indicator solution alone can signal the presence of heavy metal.

Figure 6:
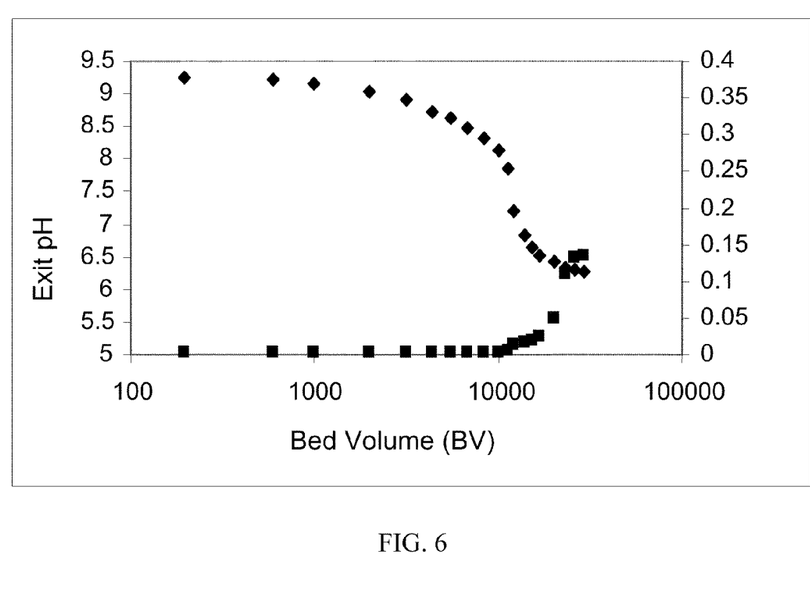
FIG. 6 is a plot showing how pH at the exit of column changed when lead of 0.4 mg/L was present in feed water [Na(I)=100 mg/L, Ca(II)=20 mg/L, Pb(II)=0.4 mg/L, pH=5.2, EBCT=0.107 min]. The drop in pH, left axis, represented by diamonds (♦), occurred much later (after 10,000 bed volumes) compared to the case when zinc was present in influent. The concentration of Pb(II) in eluent water is plotted along the right axis, and it is represented by squares (■). The horizontal axis is bed volume (BV).

The graph in FIG. 6 shows how pH dropped when lead at a concentration of 0.4 mg/L was present in the influent water along with sodium and calcium ions. The same nature of the pH drop was found, but it occurred much later compared to zinc (see FIG. 4), indicating higher sorption affinity of lead towards HIM. Note that the significant and sharp drop in pH occurs only in the presence of heavy metals such as zinc and lead, whereas the absence of heavy metals and presence of common alkaline metals like sodium and calcium have no noticeable impact on the pH. Therefore, this demonstrates that change of pH alone is an indicator for the presence of heavy metal contaminants.

In order to analyze the impact of concentration of heavy metals and also the type of heavy metals, several column studies were conducted in order to ascertain (1) the impact on pH change and time of breakthrough at different concentrations of any particular heavy metal; (2) the time and magnitude of response with respect to effluent pH for different types of heavy metals; and (3) the influence of the composition of HIM. Influent water solutions were prepared with same background of sodium and calcium, and almost identical flow rate, EBCT, etc. were maintained.

Figure 7:
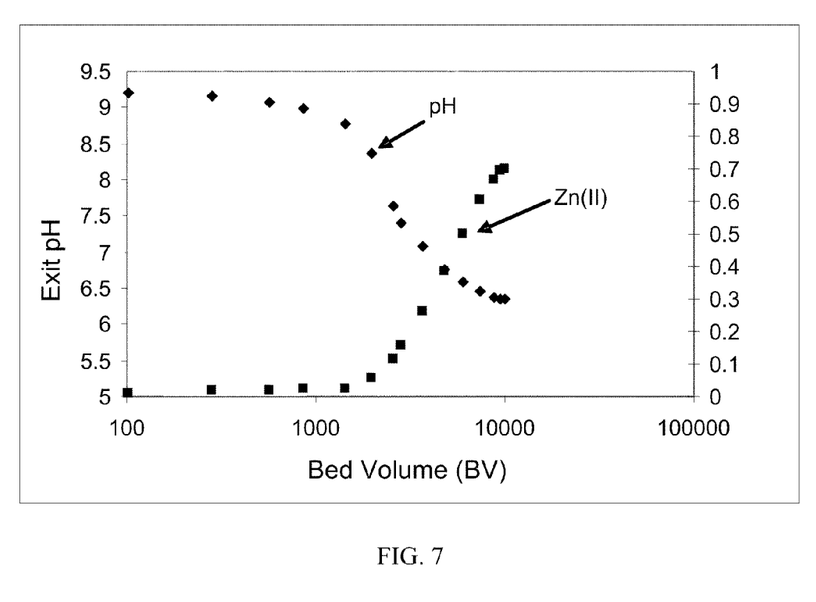
Figure 8:
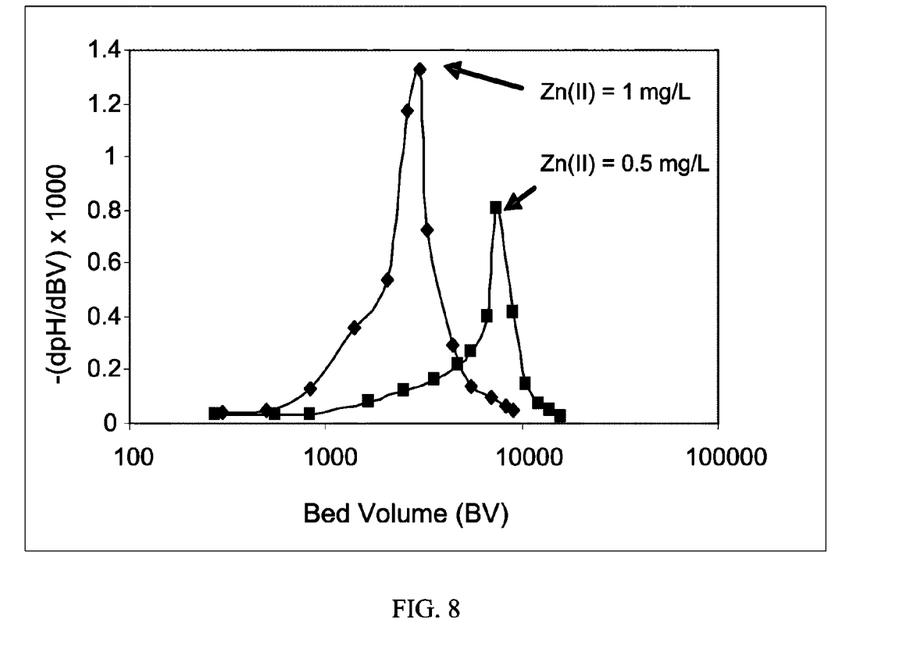
FIG. 8 is a plot showing the negative slope of the pH curve, −dpH/dBV (left axis, scale×1000), versus bed volume (horizontal axis) for two different concentrations of zinc. The two different peaks, 1.0 mg/L and 0.5 mg/L, appear at different times.

Experiments were conducted with 1 mg/L and 0.5 mg/L of zinc in the influent water samples. A plot of exit pH vs. bed volume for zinc 1 mg/L is illustrated in FIG. 7, which shows a sharp drop in pH. A comparison with FIG. 4 (plot for concentration of 0.5 mg/L zinc) reveals similar pattern, but at a concentration of 1 mg/L breakthrough occurs much earlier. Further, the rate of change of pH with respect to bed volume, i.e., the negative slope of pH breakthrough curve against bed volume, is plotted for the two different concentrations of zinc in FIG. 8, which demonstrates that the slope of a plotted pH curve gradually increases, passes through a maximum value, and drops. The plots for the two concentrations provide two different peaks at different times, characteristic to different concentration of zinc. The higher concentration produces a larger peak that occurs earlier providing a semi-quantitative measurement for zinc concentration.

Figure 9:
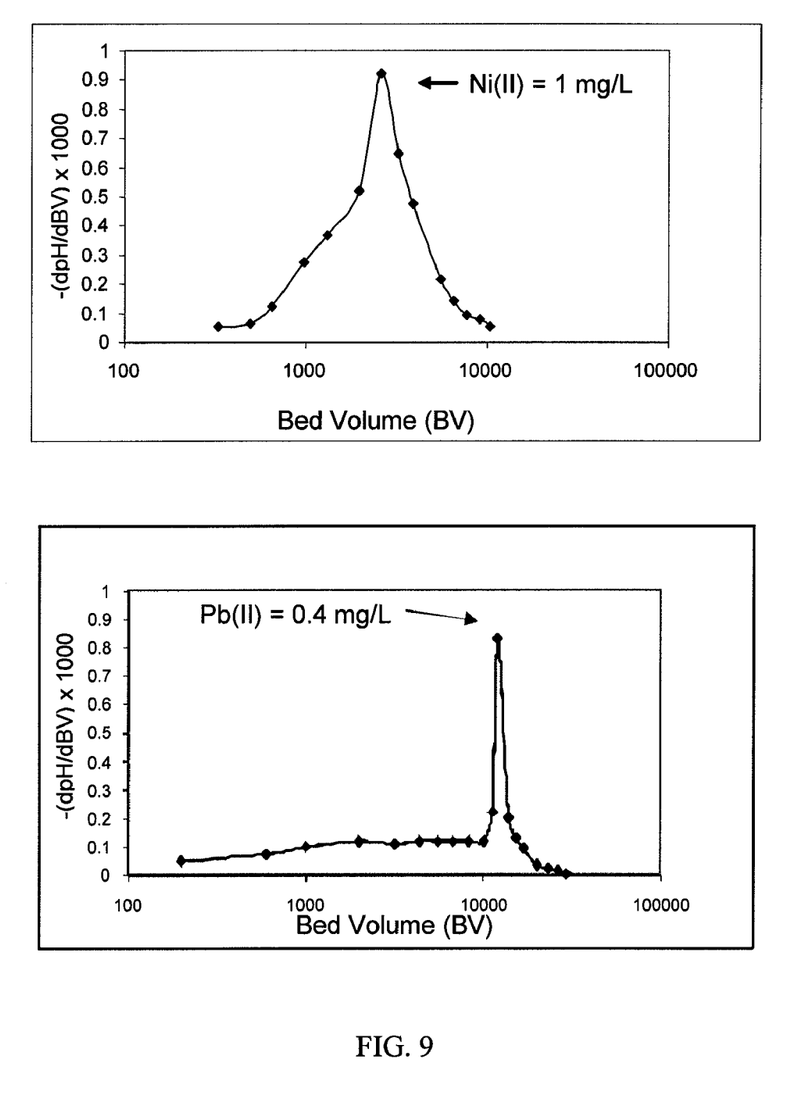
FIG. 9 includes two plots of the negative slope of the pH curve, −dpH/dBV (left axis, scale×1000), versus bed volume (horizontal axis) for nickel (Ni(II)) and lead (Pb(II)), which shows the difference in time and magnitude of response with respect to pH for these two different heavy metals.

Similar experiments with different heavy metals such as nickel, zinc, and lead in the influent each produced a sharp drop of pH similar to that of zinc. Plots of negative slope of pH curve (–dpH/dBV) against bed volume (BV) resulted in different peak heights. For example, FIG. 9 compares the slope of pH curves for nickel and lead, and it demonstrates that peaks are characteristic to the type of heavy metal present in the water sample. Thus, the time and magnitude of response with respect to pH varies for different heavy metals.

Figure 10:
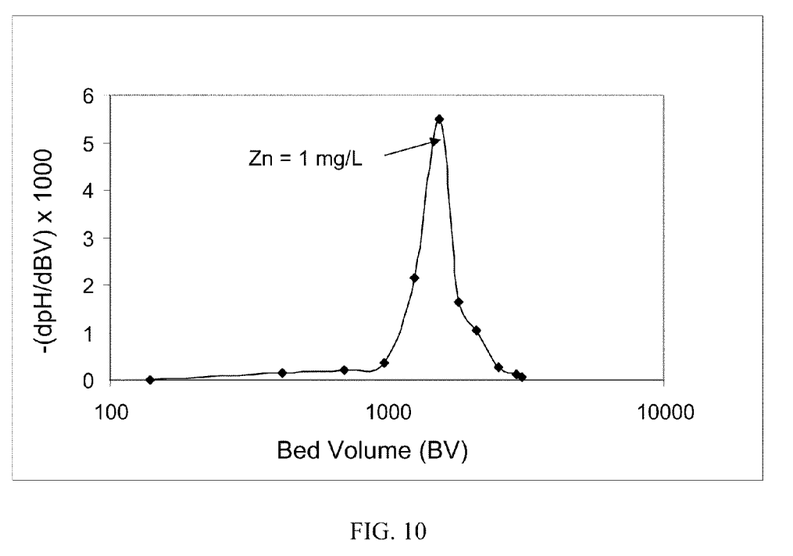
FIG. 10 is a plot of the negative slope of the pH curve, −dpH/dBV (left axis, scale×1000), versus bed volume, which shows a larger peak that appeared earlier for zinc of 1 mg/L with a varied HIM composition.

By varying the proportion of hydrated iron oxide and calcium magnesium silicate or more specifically decreasing the ratio of HFO, fresh HIM was synthesized and was useful for further experiment. Results for 1 mg/L zinc in the influent are illustrated in FIG. 10, which shows a sharper and quicker pH drop in comparison to the results shown in FIGS. 7-8, as well as a significantly larger peak. Accordingly, by varying ratio of HFO and calcium magnesium silicate, time and magnitude of response with respect to pH can be controlled for individual heavy metals.

In the foregoing experiments, the breakthrough of lead, zinc, or nickel occurred at different times due to each material's difference in sorption affinity towards HFO binding sites; lead is the most preferred and elutes (exits from the sorbent bed) much later compared to zinc and nickel, whose affinity to HFO are relatively weaker causing them to elute from HFO earlier in time.

Thus, the synthesized HIM and application methodology are useful for rapid, real-time sensing of dissolved heavy metals even at a concentration lower than 1 mg/L (about 1 ppm). The time and magnitude of response with respect to pH is characteristic to the type and concentration of the heavy metal contaminant and therefore a diagnostic semi-quantitative sensing/detection of heavy metal is possible by observing only pH changes through pH meter or even color change of indicator solution, as previously described herein.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. A method of detecting a heavy metal contaminant in water comprising steps of; providing a hybrid inorganic material synthesized from starting materials consisting of a mixture of hydrated iron oxide and calcium magnesium silicate in preselected ratios, the mixture heated to provide heat-treated fused particles of hydrated iron oxide and calcium magnesium silicate; passing a water sample through the provided hybrid inorganic material, and thereafter detecting a pH change in the water sample, and thereafter correlating the pH change to indicate the presence of a particular heavy metal in the water.

2. The method according to claim 1, wherein the pH change is an increase in pH.

3. The method according to claim 1, wherein the pH change is the slope of the pH curve versus water volume.

4. The method according to claim 1, wherein the hybrid inorganic material is in the form of a particulate packed into a bed through which water is capable of flowing.

5. The method according to claim 1, wherein the water sample is suspected of containing at least one dissolved heavy metal contaminant.

6. The method according to claim 1, wherein the flow of the water sample through the hybrid inorganic material is controlled by mechanical means.

7. The method according to claim 1, wherein the flow of the water sample through the hybrid inorganic material is controlled by gravity filtration.

8. The method according to claim 1, wherein the water sample is intended for human, animal, or agricultural use.

9. The method according to claim 1, wherein the pH change is indicative of a presence of at least one heavy metal selected from the group consisting of zinc, lead, cadmium, and nickel.

10. The method according to claim 9, wherein the at least one heavy metal is not an alkali metal or an alkaline earth metal.

11. The method according to claim 9, wherein the pH change is indicative of a concentration of at least one heavy metal.

12. The method according to claim 11, wherein the at least one heavy metal is selected from the group consisting of copper, lead, zinc, cadmium, and nickel.

13. A method of making a hybrid inorganic material comprising steps of rapidly heating a mixture of starting materials consisting of a mixture of hydrated iron oxide and calcium magnesium silicate in preselected ratios heated to produce a hybrid inorganic material consisting of heat-treated fused particles of hydrated iron oxide and calcium magnesium silicate, followed by rapidly cooling the mixture.

14. The method according to claim 13, wherein the mixture is heated to about 1800 degree C. and cooled to about room temperature in less than about two minutes.

15. The method according to claim 13, wherein the ratio of the hydrated iron oxide to the calcium magnesium silicate is about 30:70 by mass.

16. The method according to claim 13, further comprising a step of, after heating and cooling, grinding or pulverizing the mixture to thereby produce heat-treated fused particles of hydrated iron oxide and calcium magnesium silicate.

17. The method according to claim 16, further comprising a step of rinsing the heat-treated fused particles with deionized water.

18. The method according to claim 16, further comprising a step of packing the heat-treated fused particles into a bed through which water is capable of flowing.

19. A hybrid inorganic material synthesized from starting materials consisting essentially of a mixture of hydrated iron oxide and calcium magnesium silicate in preselected ratios, the mixture heated to provide a composition consisting of heat-treated fused particles of hydrated iron oxide and calcium magnesium silicate.

20. The hybrid inorganic material according to claim 19, wherein the hydrated iron oxide and the calcium magnesium silicate are present in a ratio of about 30:70 by mass.

* * * * *